United States Patent [19]

Hooper et al.

[11] 4,343,783

[45] Aug. 10, 1982

[54] DISPOSABLE ARTICLE

[75] Inventors: David C. Hooper, Ashford; George A. Johnson; Donald Peter, both of Wirral, all of England

[73] Assignee: Lever Brothers Company, New York, N.Y.

[21] Appl. No.: 3,320

[22] Filed: Jan. 15, 1979

[30] Foreign Application Priority Data

Jan. 13, 1978 [GB] United Kingdom ................ 1479/78
May 16, 1978 [GB] United Kingdom .............. 19843/78

[51] Int. Cl.³ .......................... A61K 9/70; A61L 15/03
[52] U.S. Cl. ................................. 424/28; 252/522 R; 424/65; 424/27
[58] Field of Search ............................ 424/28, 65, 27

[56] References Cited

U.S. PATENT DOCUMENTS

| | | | |
|---|---|---|---|
| 1,545,931 | 7/1925 | Weeks | 424/65 |
| 1,729,752 | 10/1929 | Southgate | 424/28 X |
| 1,813,004 | 7/1931 | Weber | 424/65 |
| 1,868,862 | 7/1932 | Washburn | 424/28 X |
| 2,024,145 | 12/1935 | Cline | 424/28 |
| 2,033,758 | 3/1936 | Cronan et al. | 424/65 X |
| 2,121,604 | 6/1938 | Lynch et al. | 424/28 X |
| 2,131,235 | 9/1938 | Randall et al. | 424/65 |
| 2,187,163 | 1/1940 | Langer | 424/28 X |
| 2,272,399 | 2/1942 | Becker et al. | 424/28 X |
| 2,875,131 | 2/1959 | Carpenter et al. | 252/522 R |
| 3,091,511 | 5/1963 | Calhoun | 424/65 X |
| 3,166,576 | 1/1965 | Markus | 424/65 |
| 3,172,817 | 3/1965 | Leupold et al. | 424/65 |
| 3,395,214 | 7/1968 | Mummert | 424/65 X |
| 3,493,650 | 2/1970 | Dunkel | 424/65 |
| 3,647,880 | 3/1972 | Blumenthal | 424/65 |
| 3,969,259 | 7/1976 | Lages | 252/107 |
| 3,975,309 | 8/1976 | Kulka et al. | 252/522 |

FOREIGN PATENT DOCUMENTS

| | | | |
|---|---|---|---|
| 7604601 | 8/1977 | Brazil . | |
| 2351927 | 4/1975 | Fed. Rep. of Germany | 424/65 |
| 2709267 | 9/1977 | Fed. Rep. of Germany | 424/65 |
| 63749 | 10/1955 | France | 424/65 |
| 8299M | 12/1970 | France | 424/65 |
| 2263300 | 3/1975 | France | 252/107 |
| 2275193 | 1/1976 | France | 424/65 |
| 550930 | 11/1956 | Italy | 424/65 |
| 52650 | 7/1965 | Norway | 424/65 |
| 425059 | 3/1935 | United Kingdom | 424/65 |
| 977570 | 12/1964 | United Kingdom | 424/65 |
| 1217682 | 12/1970 | United Kingdom | 252/522 |
| 1254198 | 11/1971 | United Kingdom | 252/522 |
| 1282889 | 7/1972 | United Kingdom | 424/65 |
| 507323 | 4/1976 | U.S.S.R. | 424/65 |

OTHER PUBLICATIONS

Klarmann, The Journal of the Soc. of Cosm. Chemist., 3/56, vol. 7, No. 2, pp. 85–105.
Ikai, Journal of Investigative Dermatology, 12/54, vol. 23, No. 6, pp. 411–422.
Drug & Cosmetic Industry, 4/69, vol. 104, No. 4, pp. 56, 58, 60, 62 & 151–153.
Brevet Special de Medicament, No. 782M, Beiersdorf, 424165.
Winter, Handbuch der Gesamten Parfumerie und Kosmetik, 2/56, pp. 329–414, 470–472; 1949, pp. 737, 739, 746 and 751.

*Primary Examiner*—Dale R. Ore
*Attorney, Agent, or Firm*—James J. Farrell; Melvin H. Kurtz

[57] ABSTRACT

A deodorant disposable porous article for use in contact with human skin or hair comprises a porous substrate impregnated with a deodorant composition having a deodorant value of from 0.50 to 3.5 as measured by the Deodorant Value Test.

14 Claims, No Drawings

DISPOSABLE ARTICLE

The invention relates to deodorant disposable articles for personal use, especially disposable articles to be worn or otherwise for use in contact with the skin or hair.

It has long been recognised that malodour originating from the human body can constitute an unpleasant experience, and that benefit could be obtained by preventing the development of malodours or by masking or otherwise obliterating malodours when they already exist.

As a means for solving this problem it is recognised that perfumes have been used as odour maskants since ancient times, and that perfumes have for this reason been incorporated into all manner of consumer articles for use in contact with skin or hair.

It is, however, recognised that the use of perfumes in this manner has its limitations, in that the duration of effectiveness can be relatively short-lived, or that offensive malodours are only partially masked.

It has now been discovered that certain mixtures of substances (some of which can be perfumery materials), hereinafter referred to as "deodorant compositions", when incorporated into articles for use in contact with human skin or hair, can provide a more effective means for preventing malodour development or for reducing the perception of malodours which are already present. It is apparent that this effect is not solely one of odour masking, since in many instances there is no detectable fragrance remaining after application of the article. Accordingly, the use of deodorant compositions in deodorant articles of the type defined represents a new operative principle.

In the course of attempts to characterise this new principal, many hundreds of substances or blends of substances have been screened for evidence of their deodorant activity.

DEFINITION OF THE INVENTION

In its widest aspect, the invention provides a deodorant disposable porous article for use in contact with human skin or hair comprising a porous substrate impregnated with from 0.001 to 10% by weight of a deodorant composition, said deodorant composition comprising from 45 to 100% by weight of deodorant components, said components having a lipoxidase-inhibiting capacity of at least 50% or a Raoult Variance Ratio of at least 1.1, said components being classified into six classes consisting of:
   Class 1: phenolic substances
   Class 2: essential oils, extracts, resins and synthetic oils
   Class 3: aldehydes and ketones
   Class 4: polycyclic compounds
   Class 5: esters
   Class 6: alcohols
provided that where a component can be classified into more than one class it is placed in the lower or lowest numbered class; said components being selected so that:
   (a) the deodorant composition contains at least five components of which at least one must be selected from each of class 1, class 2 and class 4;
   (b) the deodorant composition contains components from at least 4 of the 6 classes; and
   (c) any component present in the deodorant composition at a concentration of less than 0.5% by weight of said composition is eliminated from the requirements of (a) and (b).

The invention also provides a process for preparing a deodorant disposable porous article for use in contact with human skin which process comprises impregnating a porous substrate with an effective amount of a deodorant composition as herein defined to provide a deodorant disposable fibrous article.

The invention furthermore provides a method for suppressing human body malodour which comprises applying to the human skin a deodorant disposable porous article as herein defined.

It is a preferred property of the deodorant article of the invention that it should comprise a deodorant composition which satisfies a deodorancy test when applied to the skin of human subjects. The average amount by which body malodour should be reduced is expressed in terms of the deodorant value of the deodorant composition contained in the deodorant article. Articles of the invention accordingly preferably comprise a deodorant composition having a deodorant value of from 0.50 to 3.5. Articles in which the deodorant composition has a deodorant value of below 0.50 are outside the scope of this invention and are considered to be incapable of reducing body malodour to a significant extent.

The Deodorant Value Test

In this test the deodorant value of a deodorant composition is measured by assessing its effectiveness, when contained in a standard soap bar at a standard concentration, in reducing body malodour when the standard soap bar is used to wash the axillae (armpits) of a panel of human subjects.

The choice of a soap base is not critical to the performance of the test but as illustrative of the conduct of the test in this respect the procedure followed in the preparation of the base employed in many of the tests referred to later in this specification is included in the description of the test.

Standard soap bars are prepared as follows, all amounts given being by weight.

As soap base there is used a neutral wet sodium soap containing 63% of total fatty matter of which 82% is tallow fatty acid and 18% is coconut oil fatty acid. To a homogeneous mixture of 9000 parts of this soap base and 340 parts of free coconut oil fatty acid at 80° C. are added with mixing, 9.4 parts of a 20% aqueous solution of tetrasodium ethylenediamine tetraacetate, 2.2 parts of a 60% aqueous solution of 1-hydroxyethane-1,1-diphosphonic acid and 7.2 parts of butylated hydroxy toluene (BHT) antioxidant dissolved in a little methylated spirit and the temperature of the mass is raised to 140° C. under superatmospheric pressure. The mass is then sprayed at about 30 mm of mercury, to produce a dried soap composition which is collected and extruded at 30° C. as noodles of about 12% moisture content.

9,770 parts of the soap noodles thus obtained are mixed at ambient temperature with 150 parts of the deodorant composition to be tested, together with 30 parts of a titanium dioxide opacifier and 50 parts of a colourant suspension. The resulting mixture is milled and plodded in conventional equipment, cut into billets and stamped into bars. The deodorant composition to be tested is therefore present at the standard level of 1.5%. These bars are described as 80/20/5 soap base and consist of 80 parts tallow soap and 20 parts coconut soap, 5 parts of this soap mixture being free fatty acids expressed as coconut oil fatty acid.

Control soap bars are prepared in a similar manner except that the deodorant composition is omitted. In other respects, the control bar should only contain those additives conventionally present in personal washing products and for the purpose in the amount conventionally used in the art. For example, it is permissible as indicated in the foregoing description to include antioxidants in the control bar, but these should be present only in the amount required to stabilise the soap base.

The test is conducted as follows:

A team of 3 Caucasian female assessors of age within the range of from 20 to 40 years is selected for olfactory evaluation on the basis that each is able to rank correctly the odour levels of the series of aqueous isovaleric acid solutions listed in Table 1 below, and each is able to detect the reduction in body odour following application to the axillae of human subjects of soap containing 2% germicides, according to the procedure described in Whitehouse and Carter, Proc. Scientific Section of the Toilet Goods Association, 48, 31 (1967).

A panel of 50 human subjects for use in the test is assembled from Caucasian male subjects of age within the range of from 20 to 55 years. By screening, subjects are chosen who develop axilliary body malodour that is not unusually strong and who do not develop a stronger body malodour in one axilla compared with the other. Subjects who develop unusually strong body malodour, for example due to a diet including curry or garlic, are not selected for the panel.

For two weeks before the start of a test, the panel subjects are assigned a non-deodorant soap bar for exclusive use of bathing and are denied the use of any type of deodorant or antiperspirant. At the end of this period, the 50 subjects are randomly divided into two groups of 25. The control soap bars are then applied to the left axillae of the first group and the right axillae of the second, and the test soap bars are applied to the right axillae of the first group and the left axillae of the second.

The soap bars are applied by a technician using a standard technique in which a wet flannel is soaped with the soap bar for 15 seconds, the axilla is washed with the soaped flannel for 30 seconds, then wiped with a water rinsed flannel and dried with a clean towel. Each subject then puts on a freshly laundered shirt, and 5 hours after application the odour intensity of each subject is assessed, the left axilla of each subject being assessed before the right. The application and assessment are carried out on each of four successive days.

The odour intensity is evaluated by all three assessors who, operating without knowledge of the soap bars used for each subject or the result of evaluation of their fellow-assessors, sniff each axilla and assign a score corresponding to the strength of the odour, on a scale from 0 to 5, with 0 corresponding to no odour and 5 representing very strong odour. Before evaluation each subject stands with his arms against his side: he then raises one arm straight overhead, flattening the axilla vault and making it possible for assessor's nose to be brought close to the skin, the assessor makes an evaluation and the procedure is repeated with the other axilla.

Standard aqueous solutions of isovaleric acid which correspond to each of the scores 1,2,3,4 and 5 are provided for reference to assist the assessors in the evaluation. These are shown in Table 1 below.

TABLE 1

| Score | Odour Level | Concentrations of aqueous solution of isovaleric acid (ml/l) |
|---|---|---|
| 0 | No odour | 0 |
| 1 | Slight | 0.013 |
| 2 | Definite | 0.053 |
| 3 | Moderate | 0.22 |
| 4 | Strong | 0.87 |
| 5 | Very strong | 3.57 |

The scores recorded by each assessor for each soap bar are averaged and the average score of the test soap bars deducted from the average score of the control soap bars to give the deodorant value of the deodorant composition present in the test soap bars.

As a check that the selection of panel subjects is satisfactory for operation of the test, the average score with the control soap bars should be between 2.5 and 3.5.

More generally, deodorant values can be determined at other deodorant composition concentrations or with detergent products other than the standard soap bar using a test similar to the test described above.

Although the invention in its widest aspect provides deodorant articles comprising deodorant compositions having a deodorant value of from 0.50 to 3.5, preferred deodorant articles are those comprising deodorant compositions which have a deodorant value of at least 0.60, or 0.70, or 0.80, or 0.90, or 1.00, or 1.20, the higher the minimum value, the more effective is the article as a deodorant article as recorded by the assessors in the deodorant value test. It has also been noted that consumers, who are not trained assessors, can detect by self-assessment a noticeable reduction in body malodour where the deodorant value is at least 0.70, the higher the deodorant value above this figure, the more noticeable is the deodorant effect.

The Deodorant Composition

The characterisation of the deodorant composition of the invention presents difficulties, since it cannot be defined solely in terms of substances of specified structure and combinations in specified proportions. Nevertheless, procedures have been discovered that enable the essential materials of the deodorant compositions to be identified by tests.

The essential materials required for the formulation of deodorant compositions are those having a lipoxidase-inhibiting capacity of at least 50% or those having a Raoult variance ratio of at least 1.1, as determined by the following tests, which are designated the lipoxidase and morpholine tests respectively.

The Lipoxidase Test

In this test the capacity of a material to inhibit the oxidation of linoleic acid by lipoxidase (EC1.13.1.13) to form a hydroperoxide is measured.

Aqueous 0.2 M sodium borate solution (pH 9.0) is used as buffer solution.

A control substrate solution is prepared by dissolving linoleic acid (2.0 ml) in absolute ethanol (60 ml), diluting with distilled water to 100 ml and then adding borate buffer (100 ml) and absolute ethanol (300 ml).

A test substrate solution is prepared in the same way as the control substrate solution except that for the absolute ethanol (300 ml) is substituted the same volume of a 0.5% by weight solution in ethanol of the material to be tested.

A solution of the enzyme lipoxidase in the borate buffer and having an activity within the range of from 15,000 to 40,000 units per ml is prepared.

The activity of the lipoxidase in catalysing the oxidation of linoleic acid is first assayed spectrophotometrically using the control. An automatic continuously recording spectrophotometer is used and the increase in extinction at 234 nm (the peak of hydroperoxide) is measured to follow the course of oxidation, the enzyme concentration used being such that it gives an increase in optical density (OD) at 234 nm within the range of from 0.6 to 1.0 units per minute. The following ingredients are placed in two 3 ml cuvettes:

|  | Control (ml) | Blank (ml) |
| --- | --- | --- |
| Control substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the control cuvette last and the reaction immediately followed spectrophotometrically for about 3 minutes, with recording of the increase in optical density at 234 nm as a curve on a graph.

The capacity of a material to inhibit the oxidation is then measured using a test sample containing enzyme, substrate and a deodorant material. The following ingredients are placed in two 3 ml cuvettes.

|  | Test Sample (ml) | Blank (ml) |
| --- | --- | --- |
| Test substrate solution | 0.10 | 0.10 |
| Absolute ethanol | 0.10 | 0.10 |
| Borate buffer | 2.75 | 2.80 |
| Lipoxidase solution | 0.05 | — |

The lipoxidase solution is added to the test sample cuvette last and the course of the reaction immediately followed as before.

The lipoxidase-inhibiting capacity of the material is then calculated from the formula $100(S_1-S_2)/S_1$, where $S_1$ is the slope of the curve obtained with the control and $S_2$ is the slope of the curve obtained with the test sample, and thus expressed as % inhibition. A material that gives at least 50% inhibition in the test is hereafter referred to as having a lipoxidase-inhibiting capacity of at least 50%.

The Morpholine Test

In this test the capacity of a material to depress the partial vapour pressure of morpholine more than that required by Raoult's Law is measured. Substances that undergo chemical reaction with morpholine, for example aldehydes, are to be regarded as excluded from the test.

Into a sample bottle of capacity 20 ml is introduced morpholine (1 g) the bottle fitted with a serum cap and then maintained at 37° C. for 30 minutes for equilibrium to be reached. The gas in the headspace of the bottle is analysed by piercing the serum cap with a capillary needle through which nitrogen at 37° C. is passed to increase the pressure in the bottle by a standard amount and then allowing the excess pressure to inject a sample from the headspace into gas chromatograph apparatus, which analyses it and provides a chromatographic trace curve with a peak due to morpholine, the area under which is proportional to the amount of morpholine in the sample.

The procedure is repeated under exactly the same conditions using instead of morpholine alone, morpholine (0.25 g) and the material to be tested (1 g); and also using the material (1 g) without the morpholine to check whether it gives an interference with the morpholine peak (which is unusual).

The procedure is repeated until reproducible results are obtained. The areas under the morpholine peaks are measured and any necessary correction due to interference by the material is made.

A suitable apparatus for carrying out the above procedure is a Perkin-Elmer Automatic GC Multifract F40 for Head Space Analysis. Further details of this method are described by Kolb in "CZ-Chemie-Technik", Vol 1, No 2, 87–91 (1972) and by Jentzsch et al in "Z.Anal.-Chem." 236, 96–118 (1968).

The measured areas representing the morpholine concentration are proportional to the partial vapour pressure of the morpholine in the bottle headspace. If A is the area under the morpholine peak when only morpholine is tested and A' is the area due to morpholine when a material is present, the relative lowering of partial vapour pressure of morpholine by the material is given by $1-A'/A$.

According to Raoult's Law, if at a given temperature the partial vapour pressure of morpholine in equilibrium with air above liquid morpholine is p, the partial vapour pressure p' exerted by morpholine in a homogeneous liquid mixture of morpholine and material at the same temperature is $pM/(M+PC)$, where M and PC are the molar concentrations of morpholine and material. Hence, according to Raoult's Law the relative lowering of morpholine partial vapour pressure $(p-p')/p$ is given by $1-M/(M+PC)$, which under the circumstances of the test is $87/(87+m/4)$, where m is the molecular weight of the perfume material.

The extent to which the behaviour of the mixture departs from Raoult's Law is given by the ratio $$\frac{1 - A'/A}{87/(87 + m/4)}$$

The above ratio, which will be referred to as the Raoult variance ratio, is calculated from the test results. Where a material is a mixture of compounds, a calculated or experimentally determined average molecular weight is used for m. A material that depresses the partial vapour pressure of morpholine by at least 10% more than that required by Raoult's Law is one in which the Raoult variance ratio is at least 1.1.

A large number of materials which satisfy one or both tests is described later in this specification and these are hereafter referred to as "components", in contrast to other materials which fail both tests which are referred to as "ingredients".

Before defining the more detailed aspects of the invention so far as it relates to deodorant compositions, it is necessary to clarify some of the terms that will be employed.

A composition is a blend of organic compounds. For the purposes of this specification it is necessary to identify the "components" in the composition. This is done by first describing the composition in terms of four categories. These categories are given below. Examples of components in each category are provided.
(1) Single chemical compounds whether natural or synthetic, e.g. coumarin (natural or synthetic), iso-eugenol, benzyl salicylate. The majority of components are in this category.
(2) Synthetic reaction products (products of reaction), mixtures of isomers and possibly homolouges, e.g. α-iso-methyl inone.
(3) Natural oils, gums and resins, and their extracts, e.g. patchouli oil, geranium oil, clove leaf oil, benzoin resinoid.
(4) Synthetic analogues of category 3. This category includes materials that are not strict analogues of natural oils, gums and resins but are materials that result from attempts to copy or improve upon materials of category 3, e.g. Bergamot AB 430, Geranium AB 76, Pomeransol AB 314.

Components of Categories (3) and (4) although often uncharacterised chemically are available commercially.

Where a material is supplied or used conventionally for convenience as a mixture, e.g. p-t-Amylcyclohexanone diluted with diethyl phthalate, for the purposes of this specification two components are present, so that use of 5% of a blend of 1 part of this ketone and 9 parts of diethyl phthalate is represented as 0.5% of the ketone and 4.5% of diethyl phthalate.

It has been found advantageous in formulating the most effective deodorant composition for incorporation into the detergent product of the invention to use components that, as well as satisfying the lipoxidase or morpholine tests, satisfy further conditions. These conditions are:
(i) there must be at least five components present,
(ii) each of these components must be selected from at least four different chemical classes (to be defined below),
(iii) a component from each of classes 1,2 and 4 must be present,
(iv) at least 45%, preferably at least 50% and most preferably from 60 to 100%, by weight of the deodorant composition must comprise components,
(v) a component is not considered to contribute to the efficacy of the deodorant composition if it is present in the deodorant composition at a concentration of less than 0.5% by weight, and
(vi) a class is not considered to contribute to the efficacy of the deodorant composition if it is present in the deodorant composition at a concentration of less than 0.5% by weight.

Therefore, according to a preferred embodiment of the invention, there is provided a deodorant detergent product as herein defined in which the deodorant composition consists essentially of from about 45 to 100% by weight of ingredients, each of the components being selected from components having a lipoxidase inhibiting capacity of at least 50% and components having a Raoult variance ratio of at least 1.1, the components and ingredients being so chosen that the deodorant value of the deodorant composition is within the range 0.50 to 3.5.

Each component should be allocated to one of six classes. These classes are:
Class 1—Phenolic substances;
Class 2—Essential oils, extracts, resins, "synthetic" oils (denoted by "AB");
Class 3—Aldehydes and ketones;
Class 4—Polycyclic compounds;
Class 5—Esters;
Class 6—Alcohols.

In attributing a component to a class, the following rules are to be observed. Where the component could be assigned to more than one class, the component is allocated to the class occurring first in the order given above: for example clove oil, which is phenolic in character, is placed in Class 1 although it otherwise might have been allocated to Class 2. Similarly, 2-n-heptyl cyclopentanone which is a polycyclic ketone is attributed to Class 3 instead of Class 4.

The following are examples of deodorant components that either have a lipoxidase inhibiting capacity (LIC) of at least 50% or have a Raoult variance ratio (RVR) of at least 1.1. Their class, molecular weight (m), LIC and RVR as determined by the tests already described herein are also listed.

The nomenclature adopted for the components listed below and for the ingredients which appear in the deodorant formulations of the Examples is, so far as is possible, that employed by Steffen Arctander in "Perfume and Flavour Chemicals (Aroma Chemicals)" Volume I and II (1969) and the "Perfume & Flavour Materials of Natural Origin" (1960) by the same author. Where a component or other ingredient is not described by Arctander, then either the chemical name is given or, where this is not known (such as is the case with perfumery house specialities), then the supplier's identity can be established by reference to the appendix which appears at the end of the specification.

| | LIC | RVR | m |
|---|---|---|---|
| Class 1 - Phenolic Substances | | | |
| iso-Amyl salicylate | 95 | 1.24 | 208 |
| Benzyl salicylate | 0 | 1.58 | 228 |
| Carvacrol | 32 | 1.43 | 150 |
| Clove leaf oil | 79 | 1.43 | 164 |
| Ethyl vanillin | 100 | 1.43 | 152 |
| iso-Eugenol | 100 | 1.48 | 164 |
| LRG 201 | 100 | 1.21 | 196 |
| Mousse de chene Yugo | 98 | 1.29 | 182 |
| Pimento leaf oil | 100 | — | 165 |
| Thyme oil red | 55 | 1.37 | 150 |
| Class 2 - Essential oils, extracts, resins, "synthetic" oils (denoted by "AB") | | | |
| Benzoin Siam resinoids | 87 | — | — |
| Bergamot AB 37 | 58 | 0.97 | 175 |
| Bergamot AB 430 | 58 | 0.97 | 175 |
| Geranium AB 76 | 26 | 1.29 | 154 |
| Geranium oil | 26 | 1.29 | 154 |
| Opoponax resinoid | 96 | 1.33 | 150 |
| Patchouli oil | 76 | 1.25 | 140 |
| Petitgrain oil | 34 | 1.27 | 175 |
| Pomeransol AB 314 | 100 | — | — |
| Class 3 - Aldehydes and Ketones | | | |
| 6-Acetyl-1,1,3,4,4,6-hexamethyl-tetrahydronaphthalene | 100 | 1.03 | 258 |
| p-t-Amyl cyclohexanone | 50 | 1.10 | 182 |
| p-t-Butyl-α-methyl hydrocinnamic aldehyde | 74 | — | 204 |
| 2-n-Heptylcyclopentanone | 56 | 1.05 | 182 |
| α-iso-Methyl ionone | 100 | 1.13 | 206 |
| β-Methyl naphthyl ketone | 100 | 0.96 | 170 |
| Class 4 - Polycyclic Compounds | | | |
| Coumarin | 58 | 1.22 | 146 |
| 1,3,4,6,7,8-Hexahydro-4,6,6,7,8,8-hexamethyl cyclopenta-γ-2-benzopyran | 100 | — | 240 |
| 3a-Methyl-dodecahydro-6,6,9a-trimethylnaphtho(2,1-b)furan | 58 | 1.30 | 230 |
| β-Naphthyl methyl ether | 100 | — | 158 |
| Class 5 - Esters | | | |
| o-t-Butylcyclohexyl acetate | 52 | 1.08 | 198 |

-continued

|  | LIC | RVR | m |
|---|---|---|---|
| p-t-Butylcyclohexyl acetate | 54 | 0.98 | 198 |
| Diethyl phthalate | 79 | 1.20 | 222 |
| Nonanediol-1,3-diacetate | 33 | 1.17 | 244 |
| Nonanolide-1:4 | 92 | 0.87 | 156 |
| i-Nonyl acetate | 50 | 0.83 | 186 |
| i-Nonyl formate | 19 | 1.49 | 172 |
| Class 6 - Alcohols | | | |
| Dimyrcetol | 16 | 1.22 | 156 |
| Phenylethyl alcohol | 22 | 1.24 | 122 |
| Tetrahydromuguol | 24 | 1.23 | 158 |

It has been shown that for best results, a certain minimum average concentration of components should be present. This minimum concentration is a function of the number of classes present—the more classes present, the lower the minimum concentration. The minimum average concentration in the various situations that can apply is shown in the Table below:

| Number of classes represented in deodorant composition | Average concentration of components | |
|---|---|---|
| | minimum not less than (%) | preferably not less than (%) |
| 4 | 5 | 6 |
| 5 | 4.5 | 5.5 |
| 6 | 4.5 | 5 |

Also, it is preferred that at least 1% of each of four classes is present in the deodorant composition, but individual components which are present at a concentration of less than 0.5% are eliminated from this calculation, as is the class into which they fall if there is present no component at a concentration of at least 0.5% which falls within that class.

More specifically, the invention also provides a deodorant disposable article as herein defined wherein the amount of deodorant components in the deodorant composition present in the classes 1,2 and 4 as herein defined is at least 1%, most preferably at least 3% by weight of the deodorant composition for each class, and the amount of components present in each of at least two other classes is at least 1% by weight of the composition, provided also that any component that is present in the deodorant composition at a concentration of less than a threshold value of 0.5% by weight is eliminated from the calculation of the amounts of components in each class.

Although at least four different classes of components should preferably be represented in the deodorant composition, superior compositions can be obtained if more than four classes are represented. Accordingly, five or six classes can be represented in the deodorant composition.

It has been shown by the preparation, examination and testing of many hundreds of deodorant compositions that the best results are obtained by keeping within the aforementioned rules when selecting types and amounts of components and ingredients. For example, deodorant compositions which contain less than the minimum concentration of components of 45% are unlikely to result in a deodorant composition having a deodorant value of at least 0.50. Therefore, in preparing the best deodorant compositions of the invention, the rules for selection of components according to their classification, the representation of different classes, the amounts of each component present, bearing in mind the threshold value below which it is believed a component will not significantly contribute, are all important to observe if the best results are to be obtained.

It should be explained that components present in the deodorant article for purposes other than obtaining deodorant effects, for example an adjunct like the antioxidant, are excluded from the operation of the preceding instructions to the extent that the component is required for that other purpose. The levels at which adjuncts are conventionally present in deodorant articles is well-established for established materials and readily determinable for new materials so that the application of the above exclusion presents no difficulty.

Deodorant compositions can be incorporated in deodorant articles according to the invention, at a concentration of from about 0.001 to about 10%, preferably from 0.01 to 5% and most preferably from 0.1 to 3% by weight.

It is apparent that if less than 0.01% of a deodorant composition is employed, then use of the deodorant article is unlikely to provide a significant reduction in body malodour intensity. If more than 10% of a deodorant composition is employed, then use of the deodorant article is unlikely to further reduce body malodour intensity beyond that observed at the 10% level.

The Porous Substrate

The porous substrate can be composed of porous material such as is conventionally employed in disposable articles for human use.

The porous substrate will generally be capable of absorbing aqueous or oily body exudates or secretions. Preferably, the porous substrate is fibrous in nature, but other substrates having minute interstices through which liquid can pass can be used. When the porous substrate is fibrous, it can for example be composed of cotton or other natural cellulosic materials, or modified cellulose or cellulose derivatives. The fibrous substrate can also be of other natural fibrous material such as wool, or it can be of synthetic fibrous material such as, for example, polyesters, polyacrylates, polyamides and acetates.

The porous material, whether fibrous or non-fibrous, can be of woven or of non-woven construction.

The Disposable Porous Article

The disposable porous article formed from the porous substrate can be any article of clothing or any other article which is normally employed or used in contact with the skin, including the mucosae, or the hair of the human body.

Examples of such disposable porous articles are absorbent applique, bandages, bedpan covers, bedspreads, bibs, bras, coveralls, cushioning materials, decontamination clothing, diapers, diaper liners, drapes, facial tissues, furniture padding, garment bags, gauze, handkerchiefs, head rests, interlinings for coats, dresses, shirts, suits, liner fabric, mattress covers, medical wipes, napkins, operating room covers, packaging materials, pads, petticoats, pillow slips, stuffing and ticking, protective clothing, quilting, sanitary napkin covers and pads, santitary towels, sheets, shirts, innersoles, liners, shoulder pads, shrouds, skirts, sleeping bags, socks, sponges, surface protectors, surgical dressings, tampons, tissues, towelling, tray liners, undergarments, such as pants and vests, wash cloths, wiping cloths, wrapping material and surgical plaster casts.

Preparation of the Disposable Porous Article

The porous substrate, either before or after manufacture or shaping to form the article, can be impregnated with the deodorant composition by any convenient means. It is however preferred to spray the deodorant composition onto the porous substrate to avoid the incorporation of an excessive amount of liquid, particularly where the article is intended to be sufficiently dry when used to mop-up and absorb body secretion or exudates.

Use of Deodorant Articles

Deodorant disposable porous articles of the invention are intended to be worn or otherwise applied to the skin or hair wherever and whenever a body malodour problem is present or is likely to occur. It is apparent that at least a proportion of the deodorant composition contained in or on the porous substrate of the deodorant article will be transferred to the skin or the hair under conditions of use, so that noticeable body malodour will be suppressed or eliminated, or will otherwise fail to develop over a period of at least 5 hours or even longer.

It is also apparent that the deodorant article after use in contact with the skin or hair will be less likely to possess an offensive odour than one which does not contain a deodorant composition as herein defined, so that disposal of the article will be less offensive.

Specific Examples of Deodorant Compositions

The following deodorant compositions are examples of those which can be employed in disposable porous articles of the invention.

Deodorant Composition 1

| Components | Parts | Class | Total in class |
|---|---|---|---|
| iso-Amyl salicylate | 5.0 | 1 | |
| Benzyl salicylate | 4.0 | 1 | 10.25 |
| LRG 201 | 1.25 | 1 | |
| Bergamot AB 430 | 15.0 | 2 | |
| Geranium AB 76 | 4.0 | 2 | 20.7 |
| Opoponax resinoid | 1.7 | 2 | |
| 1,3,4,6,7,8-Hexahydro-4,6,6,7,8,8-hexamtheyl-cyclopenta-γ-2-benzopyran | 10.0 | 4 | 10.0 |
| o-t-Butylcyclohexyl acetate | 0.5 | 5 | |
| Diethyl phthalate | 3.75 | 5 | 4.25 |
| Nonanolide-1,4 | 0.2* | (5) | |
| Ingredients | | | |
| Amber AB 358 | 3.0 | | |
| Benzyl alcohol | 0.15 | | |
| Cedar atlas oil | 5.0 | | |
| Citronellol | 7.0 | | |
| Citronella oil | 16.1 | | |
| Citronellyloxyacetaldehyde | 0.5 | | |
| Hexyl aldone | 0.7 | | |
| Jasmin AB 284 | 12.0 | | |
| Orange oil sweet | 8.0 | | |
| 10-Undecen-1-al | 0.15 | | |
| Vetyvert oil | 2.0 | | |
| | 100.0 | | |
| Total amount of components | | | 45.2 |
| Number of components present | | | 9 |
| Average amount of each component | | | 5.0 |
| Number of classes represented | | | 4 |

*eliminated from calculation - below threshold value of 0.5%.

Deodorant Composition 2

| Components | Parts | Class | Total in class |
|---|---|---|---|
| Carvacrol | 3.5 | 1 | |
| Thyme oil red | 1.0 | 1 | 4.5 |
| Bergamot AB 37 | 20.0 | 2 | |
| Pomeransol AB 413 | 6.0 | 2 | 30.0 |
| Petitgrain oil | 4.0 | 2 | |
| 6-Acetyl-1,1,3,4,4,6-hexa-methyl-tetrahydro-naphthalene | 3.0 | 3 | 8.0 |
| β-Methyl naphthyl ketone | 5.0 | 3 | |
| 3a-Methyl-dodecahydro-6,6-9a-trimethyl naphtho-(2,1-b)furan | 0.25* | (4) | |
| β-Naphthol methyl ether | 9.0 | 4 | 9.0 |
| Ingredients | | | |
| Citronellyl acetate | 5.0 | | |
| Dipropylene glycol | 4.75 | | |
| Geranyl nitrile | 1.5 | | |
| Indole | 1.0 | | |
| Lemongrass oil | 3.0 | | |
| Lime AB 402 | 10.0 | | |
| Lavendin oil | 4.0 | | |
| 1-Menthol | 8.0 | | |
| Neroli AB 78 | 6.0 | | |
| Orange oil sweet | 5.0 | | |
| | 100.0 | | |
| Total amount of components | | | 51.5 |
| Number of components present | | | 8 |
| Average amount of each component | | | 6.4 |
| Number of classes represented | | | 4 |

*eliminated for calculation - below threshold value of 0.5%

Deodorant Composition 3

| Components | Parts | Class | Total in class |
|---|---|---|---|
| Mousse de chene Yugo | 1.25 | 1 | |
| Pimento leaf oil | 10.0 | 1 | 11.25 |
| Benzoin Siam resinoids | 5.0 | 2 | |
| Bergamot AB 430 | 15.0 | 2 | 25.0 |
| Geranium oil | 5.0 | 2 | |
| p-t-Amylcyclohexanone | 5.0 | 3 | |
| α-iso-Methyl ionone | 12.0 | 3 | 17.0 |
| Coumarin | 4.0 | 4 | |
| 1,3,4,6,7,8-Hexahydro-4,6,6,7,8,8-hexamethyl-cyclopenta-γ-2-benzopyran | 3.0 | 4 | 7.0 |
| Diethyl phthalate | 4.35 | 5 | 4.35 |
| Ingredients | | | |
| Hercolyn D | 12.25 | | |
| Lavandin oil | 10.0 | | |
| Musk ambrette | 3.0 | | |
| Rosenta AB 380 | 10.0 | | |
| Rose-D-oxide | 0.15 | | |
| | 100.0 | | |
| Total amount of components | | | 64.6 |
| Number of components present | | | 10 |
| Average amount of each component | | | 6.5 |
| Number of classes represented | | | 5 |

Deodorant Composition 4

| Components | Parts | Class | Total in class |
|---|---|---|---|
| Ethyl vanillin | 0.2* | (1) | |
| iso-Eugenol | 5.0 | 1 | 6.25 |
| LRG 201 | 1.25 | 1 | |

Deodorant Composition 4 -continued

| | Parts | Class | Total in class |
|---|---|---|---|
| Bergamot AB 430 | 8.0 | 2 | 15.0 |
| Patchouli oil | 7.0 | 2 | |
| 2-n-Haptylcyclopentanone | 0.5 | 3 | 5.5 |
| α-iso-Methyl ionone | 5.0 | 3 | |
| β-Naphthol methylether | 7.5 | 4 | 7.5 |
| p-t-Butylcyclohexyl acetate | 4.3 | 5 | |
| Diethyl phthalate | 8.25 | 5 | |
| i-Nonyl formate | 5.0 | 5 | 26.55 |
| Nonanediol-1,3-diacetate | 4.0 | 5 | |
| Phenylethyl phenyl acetate | 5.0 | 5 | |
| Tetrahydro muguol | 6.0 | 6 | 6.0 |
| Ingredients | | | |
| Citronella oil | 6.0 | | |
| Green Herbal AB 502 | 15.0 | | |
| Indole | 1.5 | | |
| Rosenta AB 380 | 6.0 | | |
| Sandalone | 4.0 | | |
| γ-Undecalactone | 0.5 | | |
| | 100.0 | | |
| Total amount of components | | | 66.8 |
| Number of components present | | | 14 |
| Average amount of each component | | | 4.8 |
| Number of classes represented | | | 6 |

*eliminated from calculation - below threshiold value of 0.5%

Deodorant Composition 5

| | Parts | Class | Total in class |
|---|---|---|---|
| Components | | | |
| Benzyl salicylate | 15.0 | 1 | 21.0 |
| Mousse de chene Yugo | 6.0 | 1 | |
| Bergamot AB 430 | 15.0 | 2 | 15.0 |
| 6-Acetyl-1,3,3,4,4,6-hexamethyl tetrahydro-naphthalene | 2.5 | 3 | 2.5 |
| p-t-Amylcyclohexanone | 0.06* | (3) | |
| 3a-Methyl-dodecahydro-6,6,9a-trimethyl-naphtho-2(2,1-b)furan | 0.75 | 4 | 0.75 |
| Diethyl phthalate | 8.04 | 5 | 8.04 |
| Nonanolide-1,4 | 0.2* | (5) | |
| Dimyrcetol | 16.0 | 6 | 16.0 |
| Ingredients | | | |
| Cinnamic alcohol | 5.0 | | |
| Dimethyl benzyl carbinyl acetate | 2.5 | | |
| Dipropylene glycol | 14.25 | | |
| Geraniol | 5.0 | | |
| iso-Butyl phenyl acetate | 5.0 | | |
| Methyl salicylate | 0.5 | | |
| Pelargene | 4.0 | | |
| Trichloromethyl phenyl carbinyl acetate | 0.2 | | |
| | 100.0 | | |
| Total amount of components | | | 63.29 |
| Number of components present | | | 7 |
| Average amount of each component | | | 9.0 |
| Number of classes represented | | | 6 |

*eliminated from calculation - below threshold value for a component of 0.5%

Dedorant Composition 6

| | Parts | Class | Total in class |
|---|---|---|---|
| Components | | | |
| Clove leaf oil | 10.0 | 1 | 11.25 |
| LRG 201 | 1.25 | 1 | |
| Petitgrain oil | 10.0 | 2 | 10.0 |
| p-t-Butyl- -methyl hydro cinnamic aldehyde | 15.0 | 3 | 15.0 |
| 3a-Methyl-dodecahydro-6,6-9a-trimethylnaphtho-2-(2,1-b)furan | 0.5 | 4 | 0.5 |
| o-t-Butylcyclohexyl acetate | 2.0 | 5 | |
| Diethyl phthalate | 9.25 | 5 | 21.25 |
| i-Nonyl acetate | 10.0 | 5 | |
| Phenyl ethyl alcohol | 10.0 | 6 | 10.0 |
| Ingredients | | | |
| Benzyl propionate | 4.0 | | |
| Bergamot oil | 15.0 | | |
| Dimethyl benzyl carbinyl acetate | 5.0 | | |
| iso-Butyl benzoate | 5.0 | | |
| Neroli oil | 3.0 | | |
| | 100.0 | | |
| Total amount of components | | | 68.0 |
| Number of components present | | | 9 |
| Average amount of each component | | | 7.6 |
| Number of classes represented | | | 6 |

Deodorant Value of Deodorant Compositions 1 to 6

The deodorant value of each of the deodorant compositions exemplified herein was determined by the Deodorant Value Test using the standard 80/20/5 soap base. The results were as follows:

| Deodorant composition | Average scores | | Deodorant value |
|---|---|---|---|
| | Control bar | Test bar | |
| 1 | 3.46 | 2.93 | 0.53 |
| 2 | 3.34 | 2.73 | 0.61 |
| 3 | 3.04 | 2.47 | 0.57 |
| 4 | 3.25 | 2.10 | 1.15 |
| 5 | 3.30 | 2.70 | 0.60 |
| 6 | 3.25 | 2.33 | 0.92 |

It can be seen from the above results that each of the deodorant compositions 1 to 6 had a deodorant value which was greater than 0.50 which defines the minimum deodorant value of a deodorant composition suitable for use in the deodorant articles of the invention.

The deodorant effectiveness of disposable articles can be confirmed by a simple panel test in which a team of assessors is asked to record a score, on a 0 to 5 scale, for residual body malodour for each of a panel of subjects 5 hours after use of a deodorant disposable article according to the invention. This score is compared with that derived following the use of the corresponding control article from which the deodorant composition has been omitted.

This comparative panel test can be conducted in a manner similar to the Deodorant Value Test described hereinbefore, the articles, for example, in the form of deodorant composition-impregnated pads, being applied to the axillae of the panel of 50 subjects and the assessment subsequently being carried out 'blind' by a minimum of three assessors. Unimpregnated pads are used as controls.

The results can be expressed in terms of the 'odour reduction value' of the article, rather than its 'deodorant value', since the application to the skin of a deodorant article under test and evaluation conditions does not include the 'wash-off' sequence employed when a standard soap bar is used as described hereinbefore in the Deodorant Value Test.

It should be recognised that if an odour reduction value of less than 0.50 is recorded following use of articles of the invention according to the following test method, it is indicative that insufficient deodorant composition has been transferred to the skin of the axilla rather than evidence that the article itself contains insufficient of a deodorant composition as herein defined.

Specific Examples of the Invention

The invention is illustrated by way of a specific Example, in which the porous substrate consisted of rectangular fibrous tissue paper pads 5 cm×8 cm and 0.2 mm thick. These pads were impregnated with a deodorant composition by immersing them in a liquid formulation containing the Deodorant Composition 2 as described herein.

The liquid formulation contained the following ingredients in the amounts stated:

|  | % by weight |
|---|---|
| Octyl phenol ethoxylated (Texofor FP 85) | 5 |
| Sodium lauryl ether sulphate (27% active - Empicol ESB 3) | 35 |
| Hexylene glycol | 20 |
| Deodorant Composition 2 | 1 |
| Deionised water | to 100 |

The formulation was prepared by mixing the deodorant composition and Texofor into the hexylene glycol. The mixture so obtained was added to the water and finally the Empicol was added with further stirring.

The tissue squares were immersed in this formulation to provide a loading of 4 g formulation per g tissue.

Control tissue pads immersed in the above formulation from which the deodorant composition had been omitted were also prepared.

The test and control pads were applied to the axillae of a panel of 50 subjects and the assessment carried out 5 hours later as described herein. It was estimated that 0.25 g of the spray formulation (containing 0.0025 g of the deodorant composition) had been transferred to the skin of the axilla.

The results were as follows:

|  | Control pads | Test pads |
|---|---|---|
| Average scores | 2.48 | 0.56 |
| Odour reduction value |  | 1.92 |

APPENDIX

The following glossary provides further information, including the suppliers' names, which will aid identification of some of the aforementioned deodorant components and ingredients.

| | |
|---|---|
| Dimyrcetol: | Dimyrcetol (IFF) |
| Hercolyn D: | Tetrahydro abietate + dihydro abietate (HP) |
| LRG 201: | Oakmoss speciality (RB) |
| Pelargene: | Pelargene (PPL) |
| Rose-D-Oxide: | Rose oxide synthetic (PPL) |
| Sandalone: | Sandalone (PPL) |
| Perfume Houses | |
| HP: | Hercules Powder Co. |
| IFF: | International Flavour & Fragrances Inc. |
| RB: | Roure Bertrand |
| PPL: | Proprietary Perfumes Limited |

All materials which are classified by a name and number, such as those having the 'AB' notation, are obtainable from Proprietary Perfumes Limited.

What is claimed is:

1. A deodorant disposable porous article for use in contact with human skin, comprising a porous substrate impregnated with from 0.001 to 10% by weight of a deodorant composition having a deodorant value of from 0.50 to 3.5 as measured by the Deodorant Value Test; said deodorant composition comprising from 45 to 100% by weight of deodorant components, said components having a lipoxidase-inhibiting capacity of at least 50% or a Raoult variance ratio of at least 1.1, said components being classified into six classes consisting of:
   Class 1: phenolic substances
   Class 2: essential oils, extracts, resins and synthetic oils
   Class 3: aldehydes and ketones
   Class 4: polycyclic compounds
   Class 5: esters
   Class 6: alcohols, provided that where a component can be classified into more than one class, it is placed in the lower or lowest numbered class;
   said components being so selected that
   (a) the deodorant composition contains at least five components of which at least one must be selected from each of class 1, class 2 and class 4;
   (b) the deodorant composition contains components from at least 4 of the 6 classes; and
   (c) any component present in the deodorant composition at a concentration of less than 0.5% by weight of said composition is eliminated from the requirements of (a) and (b).

2. The deodorant article of claim 1 wherein the deodorant composition has a deodorant value of from 0.90 to 3.5 as measured by the Deodorant Value Test.

3. The deodorant article of claim 1 wherein the deodorant composition has a deodorant value of from 1.20 to 3.5 as measured by the Deodorant Value Test.

4. The deodorant article of claim 1 wherein the amount of deodorant components present in said class comprising phenolic substances and said class comprising essential oils, extracts, resins and synthetic oils and said class comprising polycyclic compounds, is at least 1% by weight of the deodorant composition for each of said classes, and the amount of deodorant components present in said further class chosen from the remaining three classes is at least 1% by weight of the deodorant composition.

5. The deodorant article of claim 1 wherein the average concentration of all such components present is at least 5% by weight where four of said classes is represented, or at least 4.5% by weight where five or six of said classes is represented.

6. The deodorant article of claim 1 wherein the amount of deodorant components present in said class comprising phenolic substances and said class comprising essential oils, extracts, resins and synthetic oils and said class comprising polycyclic compounds, is at least 3% by weight of the deodorant composition for each of said classes and the amount of deodorant components present in said further class chosen from the remaining three classes is at least 3% by weight of the deodorant composition.

7. The deodorant article of claim 1 wherein at least five of the classes is represented.

8. The deodorant article of claim 1 wherein all six classes are represented.

9. The deodorant article of claim 1 which is a sanitary towel.

10. The deodorant article of claim 1 which is a tampon.

11. The deodorant article of claim 1 which is a napkin.

12. A process for preparing the deodorant article of claim 1 which comprises impregnating a porous substrate with an effective amount of a deodorant composition to provide a deodorant disposable article.

13. A method for suppressing human body malodour which comprises applying to the skin or hair the deodorant disposable article of claim 1.

14. The deodorant article of claim 1 wherein the said deodorant components are chosen from:

Class 1—Phenolic substances
  iso-Amyl salicylate
  Benzyl salicylate
  Carvacrol
  Clove leaf oil
  Ethyl vanillin
  iso-Eugenol
  LRG 201
  Mousse de chene Yugo
  Pimento leaf oil
  Thyme oil red Class 2—Essential oils, extracts, resins, "synthetic" oils (denoted by "AB")
  Benzoin Siam resinoids
  Bergamot AB 37
  Bergamot AB 430
  Geranium AB 76
  Geranium oil
  Opoponax resinoid
  Patchouli oil
  Petitgrain oil
  Pomeransol AB 314

Class 3—Aldehydes and ketones
  6-Acetyl-1,1,3,4,4,6-hexamethyltetrahydronaphthalene
  p-t-Amyl cyclohexanone
  p-t-Butyl-$\alpha$-methyl hydrocinnamic aldehyde
  2-n-Heptyl cyclopentanone
  $\alpha$-iso-Methyl ionone
  $\beta$-Methyl naphthyl ketone Class 4—Polycyclic compounds
  Coumarin
  1,3,4,6,7,8-Hexahydro-4,6,6,7,8,9-hexamethyl cyclopenta-$\gamma$-2-benzopyran
  3a-Methyl-dodecahydro-6,6,9a-trimethylnaphtho(2,1-b)furan
  $\beta$-Naphthyl methyl ether Class 5—Esters
  o-t-Butylcyclohexyl acetate
  p-t-Butylcyclohexyl acetate
  Diethyl phthalate
  Nonanediol-1,3-diacetate
  Nonanolide-1:4
  i-Nonyl acetate
  i-Nonyl formate Class 6—Alcohols
  Dimyrcetol
  Phenylethyl alcohol
  Tetrahydromuguol.

* * * * *